(12) United States Patent
Singh et al.

(10) Patent No.: US 11,660,031 B2
(45) Date of Patent: May 30, 2023

(54) MEASURING RESPONSES TO SOUND USING PUPILLOMETRY

(71) Applicant: University of Oregon, Eugene, OR (US)

(72) Inventors: Avinash Deep Bala Singh, Eugene, OR (US); Terry Takeshi Takahashi, Eugene, OR (US)

(73) Assignee: University of Oregon, Eugene, OR (US)

( * ) Notice: Subject to any disclaimer, the term of this patent is extended or adjusted under 35 U.S.C. 154(b) by 569 days.

(21) Appl. No.: 16/785,439

(22) Filed: Feb. 7, 2020

(65) Prior Publication Data

US 2020/0253526 A1   Aug. 13, 2020

Related U.S. Application Data

(60) Provisional application No. 62/802,607, filed on Feb. 7, 2019.

(51) Int. Cl.
| | | |
|---|---|---|
| *A61B 5/16* | (2006.01) |
| *A61B 5/00* | (2006.01) |
| *A61B 3/14* | (2006.01) |
| *A61B 3/11* | (2006.01) |

(52) U.S. Cl.
CPC ............ *A61B 5/163* (2017.08); *A61B 5/0075* (2013.01); *A61B 5/742* (2013.01); *A61B 5/7405* (2013.01); *A61B 3/112* (2013.01); *A61B 3/14* (2013.01); *A61B 2503/04* (2013.01)

(58) Field of Classification Search
CPC .. A61B 5/00; A61B 5/16; A61B 5/163; A61B 5/0075; A61B 5/7405; A61B 5/742; A61B 5/40; A61B 3/11; A61B 3/10; A61B 3/112; A61B 3/14; A61B 3/113; A61B 3/032; A61B 3/145; A61B 2503/04
USPC ....... 351/206, 202, 209, 210, 221, 222, 237, 351/239, 243, 246; 600/473, 318, 558
See application file for complete search history.

(56) References Cited

U.S. PATENT DOCUMENTS

| | | | |
|---|---|---|---|
| 8,807,753 B2 * | 8/2014 | Maddess ................ | A61B 5/163 351/209 |
| 9,414,745 B2 | 8/2016 | Neice | |
| 9,763,572 B2 | 9/2017 | Sadhasivam | |
| 10,034,605 B2 | 7/2018 | Holt | |

(Continued)

OTHER PUBLICATIONS

Wetzel et al, "Infant and adult pupil dilation in response to unexpected sounds"; Developmental Psychobiology, Oct. 27, 2015 (Year: 2015).*

(Continued)

*Primary Examiner* — Jie Lei
(74) *Attorney, Agent, or Firm* — Lumen Patent Firm

(57) ABSTRACT

A method is disclosed for testing hearing in infants based on pupil dilation response. It does not require sedation or depend on subjective judgments of human testers. Pupil dilation response to sound is measured by presenting on a display a visually engaging video containing periodic changes; presenting sounds synchronized with the periodic changes of the video; recording images from a camera directed in front of the display, where the camera is sensitive to infrared wavelengths; processing the images to measure pupil sizes; and processing the measured pupil sizes to determine, statistically, the presence of a pupil dilation response to the sounds.

7 Claims, 4 Drawing Sheets

(56) References Cited

U.S. PATENT DOCUMENTS

2014/0186806 A1 7/2014 Hallowell
2015/0116665 A1 4/2015 Finkel

OTHER PUBLICATIONS

Liao et al "Human Pupillary Dilation Response to Deviant Auditory Stimuli: Effects of Stimulus Properties and Voluntary Attention", Frontiers in Neuroscience, vol. 10, Article 43, Feb. 17, 2016. (Year: 2016).*

Liao et al., Human Pupillary Dilation Response to Deviant Auditory Stimuli: Effects of Stimulus Properties and Voluntary Attention, Front. Neurosci., Feb. 17, 2016.

McAnany et al., iPhone-based Pupillometry A Novel Approach for Assessing the Pupillary Light Reflex, Optometry and Vision Science: Oct. 2018—vol. 95—Issue 10—p. 953-958.

Martínez-Ricarte et al., Infrared pupillometry. Basic principles and their application in the non-invasive monitoring of neurocritical patients, Neurología (English Edition) vol. 28, Issue 1, Jan.-Feb. 2013.

Chang, et al., Infrared Video Pupillography Coupled with Smart Phone LED for Measurement of Pupillary Light Reflex, Front Integr Neurosci. 2017; 11: 6.

Bala et al., Human Auditory Detection and Discrimination Measured with the Pupil Dilation Response, Journal of the Association for Research in Otolaryngology, Dec. 2019.

Kidd et al., The Goldilocks Effect: Human Infants Allocate Attention to Visual Sequences That Are Neither Too Simple Nor Too Complex, PLoS ONE 7(5):e36399—May 2012.

Bala et al., Infant hearing assessed using the Pupil Dilation Response, Abstracts of the 41st Annual MidWinter Meeting of the Association for Research in Otolaryngology, Feb. 9, 2018, p. 353.

Bala et al., Pupillary dilation response as an indicator of auditory discrimination in the barn owl, J Comp Physiol A (2000) 186: 425-434.

Bala et al., Prediction of auditory spatial acuity from neural images on the owl's auditory space map, Nature | vol. 424 | Aug. 14, 2003, p. 771.

Bala et al., Auditory Spatial Acuity Approximates the Resolving Power of Space-Specific Neurons, PLoS ONE, Aug. 2007 | Issue 8 | e675.

Spitzer et al., Auditory spatial discrimination by barn owls in simulated echoic conditions, J. Acoust. Soc. Am. 113 (3), Mar. 2003.

The Joint Committee on Infant Hearing. Year 2019 Position Statement: Principles and Guidelines for Early Hearing Detection and Intervention Programs. Journal of Early Hearing Detection and Intervention 2019; 4(2).

* cited by examiner

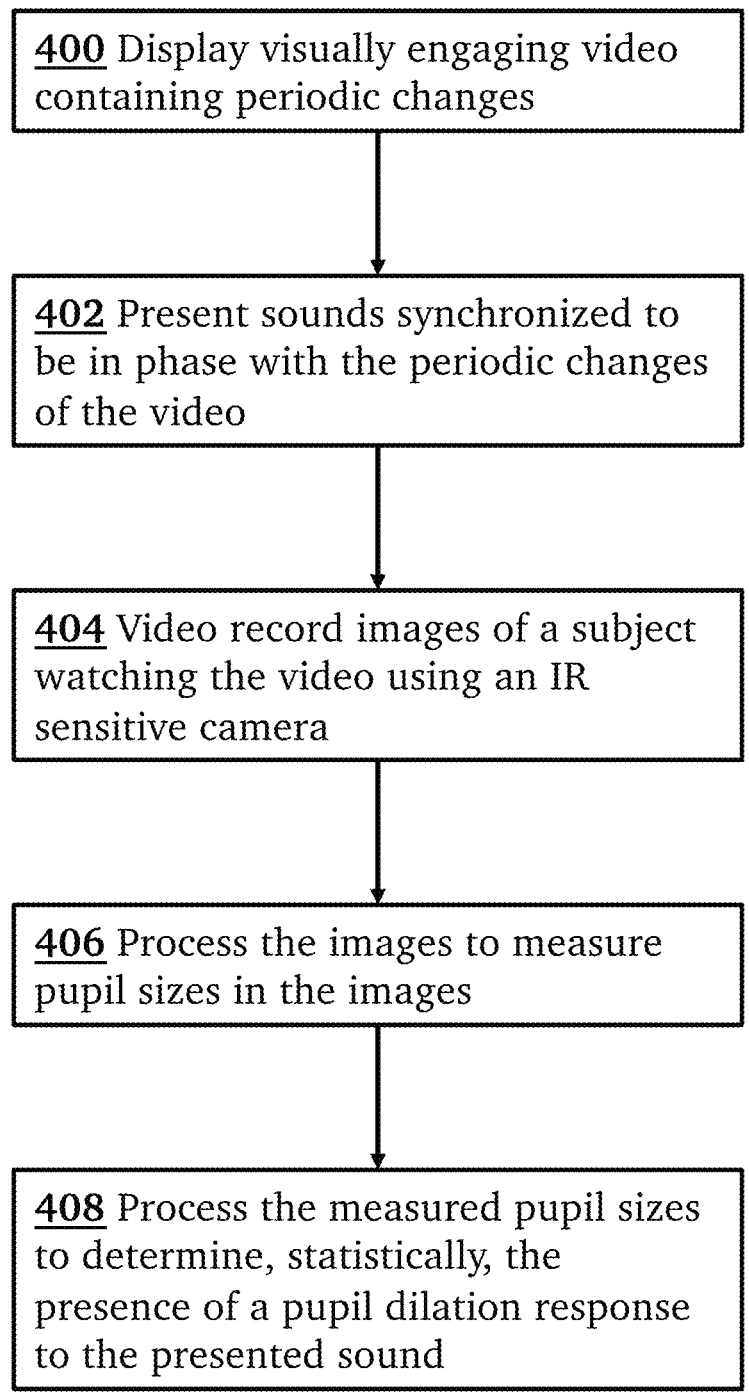

MEASURING RESPONSES TO SOUND USING PUPILLOMETRY

CROSS-REFERENCE TO RELATED APPLICATIONS

This application claims priority from U.S. Provisional Patent Application 62/802,607 filed Feb. 7, 2019, which is incorporated herein by reference.

FIELD OF THE INVENTION

The present invention relates generally to pupillometry systems, methods, and devices. More specifically, it relates to techniques for using quantitative pupillometry to measure responses to sound.

BACKGROUND OF THE INVENTION

During the first 24 months of life, infants learn the sounds of their language. Hearing is therefore critical. Early identification of hearing loss has a significant impact on maintaining normal language development, leading to the 1-3-6 guidelines of the Joint Committee on Infant Hearing (2019), which recommend that infants be screened by 1 month, diagnosed by 3 months, and receive interventions by 6 months. Current diagnostic tests involve measuring the electrical activity in the inner ear and brainstem and/or conditioning an infant to react to a test sound. However, early testing using these methods is impractical for the following reasons.

The measurement of electrical activity, or the auditory brainstem response (ABR), requires an infant to be still. Infants, especially those over 2 months, are often too active and must be sedated to conduct an ABR. The use of sedation has significant disadvantages and complications. In younger infants, ABR can be measured while asleep, but such measurements are often interrupted by waking, resulting in diagnoses based on partial data.

ABR is not widely accessible, especially if sedation is involved. Expertise required to administer the ABR and the facilities for its measurement tend to be confined to major urban centers, raising logistical difficulties for patients who live far from them. Consequently, significant numbers of infants miss the recommended 3 month deadline for diagnosis, which is termed 'loss-to-follow-up'.

The behavioral test, or visual reinforced audiometry (VRA), requires the conditioning of an infant to look toward the sound source or otherwise visibly react when a sound is presented, requiring that infants be 9 months or older, which is significantly older than the recommended 3 month guideline. VRA is labor-intensive, requiring multiple personnel who present the test sounds, draw and maintain an infant's attention, and infer the detection of the sound from the infant's behavior.

In VRA, whether or not the infant reacted to a presented sound is decided subjectively. Test conclusions may thus differ when the observers are different. Moreover, an intervention like a hearing aid or cochlear implant requires confirmation from an ABR session, reducing the utility of the VRA as a stand-alone diagnostic test.

In the standard Hughson-Westlake hearing tests, patient responses like a button press, raised hand, or verbal response are used to assess detection of brief test signals such as tones of different frequencies and amplitudes. Because of its reliance on voluntary responses, Hughson-Westlake audiometry is not suitable for patients that cannot follow instructions reliably, such as pre-lingual infants. Thus, rather than a standard test applicable across all ages, children are tested instead using a battery approach, with a variety of age-specific tests.

BRIEF SUMMARY OF THE INVENTION

The present description provides a method to assess hearing, based on a sound-elicited pupil dilation response (PDR). The method can identify hearing loss in infants quickly and without need for sedation or contact with the infant. The method can be adapted to test the discrimination of complex sounds, such as those used in language, that are not typically tested in the clinic. It can be applied to incapacitated adults and children of all ages, including newborns. Finally, it provides an objective hearing test, the results of which are not influenced by subjective judgments of testers.

A periodic animation is displayed to attract and maintain the gaze of a subject toward one or more cameras that capture images of eyes while sounds are presented at a particular phase of the periodic animation. A computer processes the images to detect changes in pupil size to determine whether the subject's pupils dilated, thus detecting a sound-evoked PDR. The technique can also be used to determine whether a subject discriminated between two complex sounds, such as phonemes.

The technique is especially useful in young active children (3-24 month) as a rapid screen for hearing loss that requires no sedation or behavioral conditioning.

In one aspect, the invention provides a method for measuring PDR to sound, the method comprising: presenting on a display to a subject a visually engaging video containing periodic changes; presenting to the subject sounds synchronized with the periodic changes of the video; recording images from a camera directed toward the subject, where the camera is sensitive to infrared (IR) wavelengths; processing the images to measure pupil sizes; and processing the measured pupil sizes to determine, statistically, the presence of a PDR to the sounds.

Preferably, the visually engaging video is selected to have sufficiently constant luminance to avoid pupil contraction responses. Preferably, the visually engaging video is selected to be sufficiently engaging such that a child's gaze remains focused on the animation during a majority of a predetermined examination time. Preferably, the visually engaging video includes periodic patterns sufficiently repetitive to cause habituation. Preferably, the sounds are selected to cause a PDR without causing a startle response. Preferably, processing the images to measure pupil sizes comprises tracking pupil location from frame to frame, extracting major and minor axes of the pupil, identifying head and eye movements, and adjusting pupil size and shape to compensate for the identified movements. Preferably, processing the measured pupil sizes to determine the presence of a PDR comprises comparing pupil sizes in trial periods with presented sounds against pupil sizes in trial periods without presented sounds.

BRIEF DESCRIPTION OF THE SEVERAL VIEWS OF THE DRAWINGS

FIG. 4 is an overview of the steps of a method for measuring sound-elicited PDR according to an embodiment of the invention.

DETAILED DESCRIPTION OF THE INVENTION

The present inventors have discovered a method for detecting the PDR evoked by sounds, enabling for the first time, a simple auditory test for nonverbal subjects. The PDR in humans is a short-latency (0.25 s) dilation of the pupil in response to novel stimuli. The PDR is a component of the Pavlovian orienting response, which includes covert behaviors such as a change in heart and breathing rates and more overt behaviors such as the turning of the head and eyes toward the stimulus. The PDR differs from dilations to changes in lighting or to exertion of mental effort, in having a shorter latency and time-to-maximum. Note that a PDR is evoked by salient stimuli at amplitudes ordinarily encountered. Very loud sounds (over 90 dB $SPL_A$), by contrast, evoke a protective response called the startle reflex, which leads to blinking and withdrawal from the source rather than dilation and orientation.

Figure 1A:
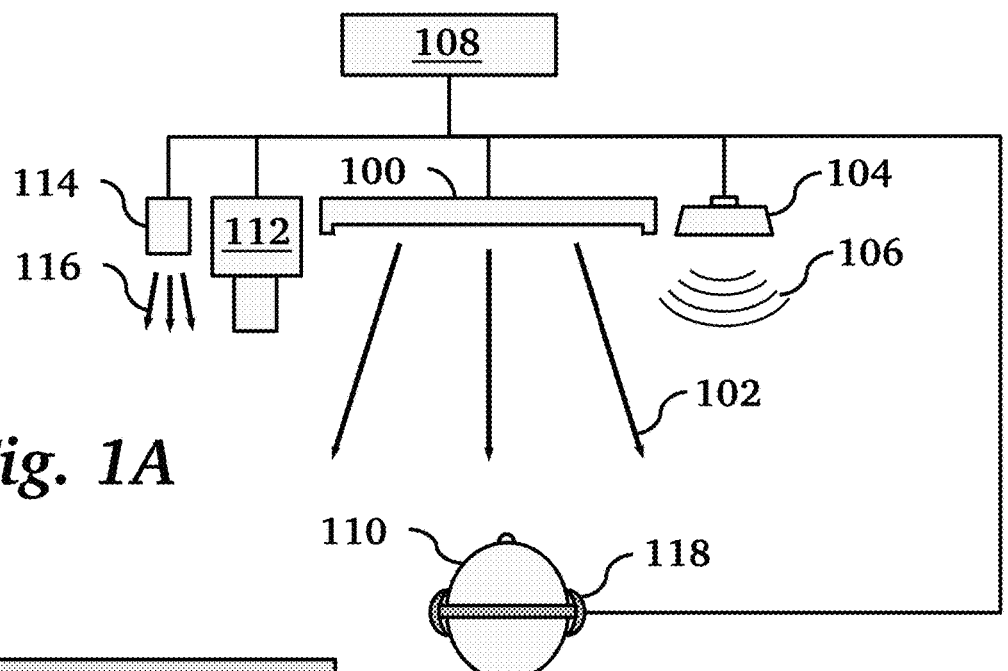
FIG. 1A is a schematic diagram of a device for measuring sound-elicited PDR according to an embodiment of the invention.

In one embodiment, the invention provides a device for detecting the PDR to sounds, as illustrated in FIG. 1A. The device includes a display 100 for displaying a video image 102 and a speaker (loudspeaker 104 or headphones 118) for generating sounds 106. The speaker and display are controlled by a computer processor 108. The device also includes a digital video camera 112 that is sensitive to IR wavelengths and, preferably, a spotlight 114 generating IR light 116. Preferably, the camera 112 is positioned above or below the center of display 100. Processor 108 controls the spotlight 114 and records video data from camera 112. The display 100, speaker 104, camera 112, and spotlight 114 are all arranged to be oriented toward a predetermined location where a human subject 110 will be seated, facing toward the display 100 and in the field of view of the camera 112. The display size and position are preferably selected so that the displayed video image 102 fills at most 20° of the subject's visual field of view. The device may be realized as a laptop or tablet computer with integrated display and camera. Alternatively, it may be realized as a desktop computer or microcomputer with display and camera as external peripheral devices.

During an auditory examination, the device is preferably located in a quiet room with constant ambient lighting. The device is positioned in front of a seat from which a subject 110 may comfortably view the display 100 while in view of the camera 112. If the subject is an infant, the child may be placed in a car seat or a parent's lap, facing the display 100 and video camera 112. The use of IR-sensitive camera and IR spotlight help provide good image contrast between the pupil and iris, even in subjects with dark irises.

Traditionally, gaze tracking systems that employ similar hardware have required subjects head to be held still via bite bars, or combinations of chin and forehead-rests. In addition, the subject was asked to keep their gaze directed toward a single point, or on events of interest. However, subjects who cannot communicate or cannot understand instructions are usually not testable, since they would be required to have their heads restrained against their will. Further, such subjects cannot be instructed to look in a particular direction, nor can they hold their gaze still. We discovered that an age-matched animation attracts their attention for several minutes at a time, during which their heads and gaze are sufficiently still that pupil size can be accurately computed using a combination of methods (listed below). Thus, for example, a child can be tested in a parent's lap.

Figure 1B:
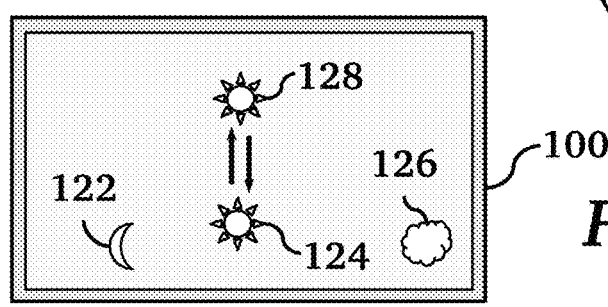
FIG. 1B is a schematic diagram illustrating an engaging periodic animation according to an embodiment of the invention.

During the examination of an infant, the display presents a simple animation having periodic changes, such as a periodic pattern of motion. The periodic animation is selected to have a substantially temporally constant total luminance in order to avoid a pupillary light response, i.e., a change in pupil size triggered by changes in the amount of incident luminance. The animation is designed to be sufficiently engaging to the child's attention that the child's gaze remains focused on the animation during a majority of the examination time. In one embodiment, illustrated in FIG. 1B, the animation shown on the display 100 includes colorful icons or images of toys or other objects 122, 124, 126 dispersed along the lower third of the monitor, which are animated to rise and fall once every period. The duration of one period is preferably 2-5 seconds. A different image may move during each trial period. At the beginning of a trial period, one image or icon 124 is animated as described above, rises to a pre-determined height 128, remains there for a second, then descends until it returns to its starting position. The number of images, their rate of movement, and the number that move simultaneously allow us to tailor the complexity of the animation to specific ages (Kidd et al, 2012).

Figure 1C:
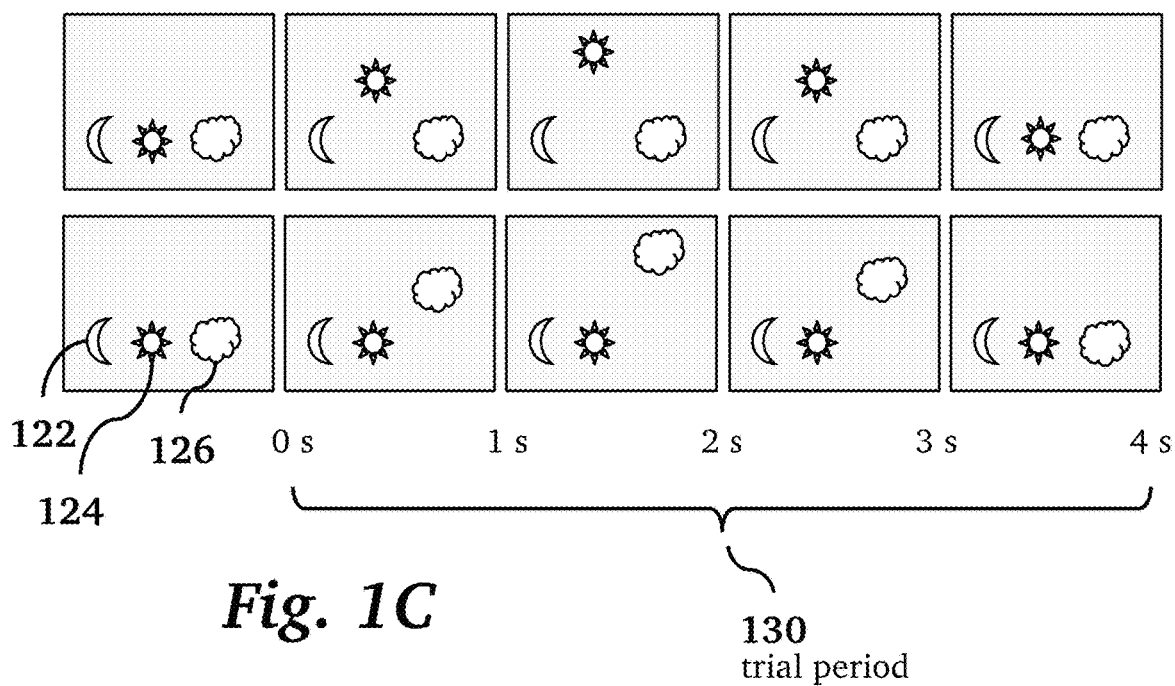
FIG. 1C is a schematic diagram illustrating frames of an engaging periodic animation according to an embodiment of the invention.

As further illustrated in FIG. 1C, the three objects 122, 124, 126 are positioned near the bottom of the screen prior to the start of each trial period. During 0-1 seconds of a trial, one of the objects rises up at a constant speed. During 1-2 seconds of the trial, the object remains still at its apex. During 2-3 seconds of the trial, the object descends to its original position at the bottom of the screen. Finally, during 3-4 seconds of the trial, all objects remain stationary at the bottom. The top row illustrates a trial in which the sun rises and falls, while the second row illustrates a trial in which the cloud rises and falls. This pattern of rising and falling objects is repeated each trial period for a randomly selected one of the three objects, except that no single object will rise in more than three consecutive trials.

More generally, a suitable animation for the purposes of the present invention is a periodic animation that engages the subject's attention while not itself stimulating PDR. A sufficiently engaging animation will hold the subject's attention for a majority of the time during the examination. Animations that are too simple (e.g., too few objects or objects moving too slowly) or too complex (e.g., too many objects on screen or objects moving too fast) fail to capture and retain an infant's attention. An animation is defined as being engaging when the complexity and rate of change in the animation is selected between these extremes such that the infant will spend more time looking at the display than away from it. Further guidance can be found in prior research (Kidd et al. 2012). In the case of adult subjects, the animation may be adapted in complexity and amount of movement.

The repeated, periodic movements in the animation cause the subject to habituate to the visual stimulus, so that any PDR elicited by the animation itself is quickly attenuated. If the visual input from the animation is too complex and changing too often, the subject may constantly be stimulated, leading to a persistent PDR evoked by the animation itself, drowning out the desired sound-evoked PDR. In other words, the animation is selected to be sufficiently engaging to retain the subject's attention while not being so stimulating that it leads to PDR that interferes with the response to the sound. To strike this balance, the animation periodically repeats a pattern of movement, e.g., an object rising on the screen, pausing at the zenith, then descending back to the starting point, but includes variations in order to keep the content engaging, e.g., changes in the shape, color, location, and type of object represented on screen.

Synchronized to the periodicity of the animation (i.e., in phase with the animation), brief sounds (or, in some trials, periods of silence) are presented. All the while, the video camera records images of the subject's eye(s).

Figure 2A:
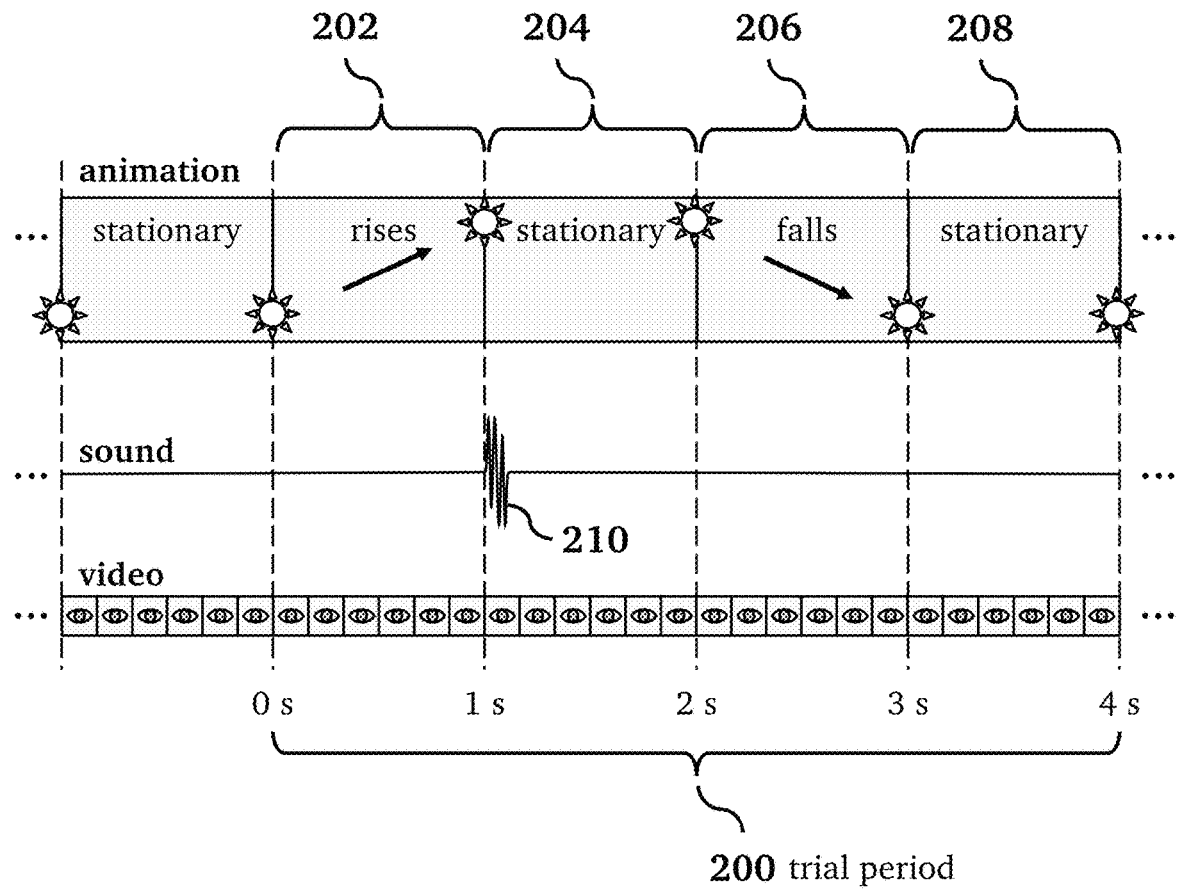
FIG. 2A is a timeline illustrating synchronized animation, sound, and video events during intervals of a trial according to an embodiment of the invention.

FIG. 2A shows the synchronized sequence of animation (top), test-sound presentation (middle), and video capture (bottom) events for a single trial period 200. The trial period in this example has a duration of 4 seconds, comprising four intervals of 1 second each. In the first interval 202 from 0-1 seconds of the trial, an object rises. In the second interval 204 from 1-2 seconds of the trial, the object remains stationary at its zenith. At the beginning of this interval, a test sound 210 lasting 0.1 seconds is presented. Alternatively, if the trial is a catch trial, no sound is presented. In the third interval 206 from 2-3 seconds of the trial, the object descends. In the fourth interval 208 from 3-4 seconds of the trial, the object is stationary at its nadir.

The amplitude of each test sound is typically ramped up in 5 or 10 ms to avoid spectral artifacts (e.g., clicks). These stimuli could in some cases resemble sounds used in typical hearing tests, for example, 100 ms bursts of reproducible narrowband noises (approximately ⅓ octave) with a center frequency in the range 0.5-8 kHz (e.g., 2 kHz) presented at 20-70 dB $SPL_A$, a range consistent with current pediatric audiology practice.

Figure 2B:
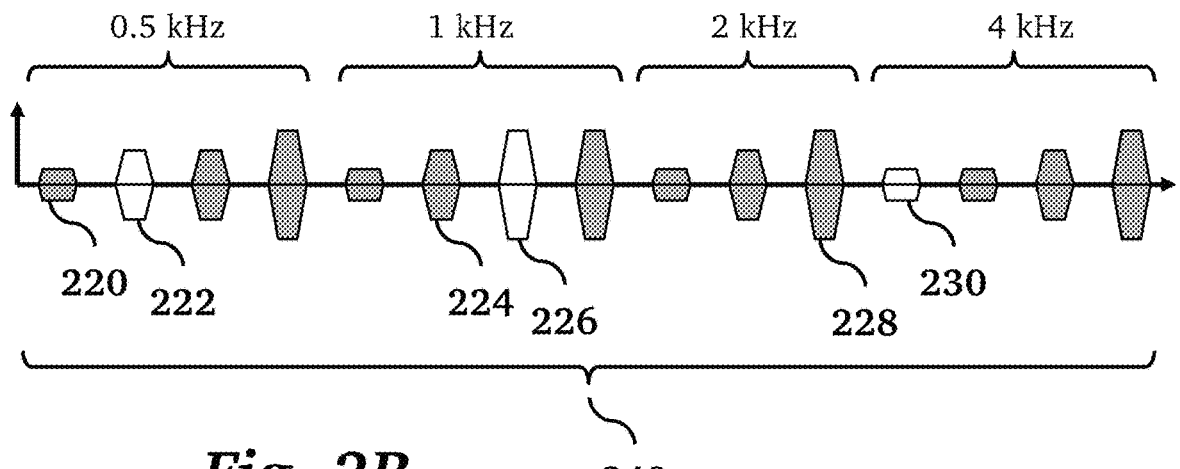
FIG. 2B is a graph of amplitude versus time illustrating a sequence of sound and catch trials according to an embodiment of the invention.

During an examination, a sequence of trials following a similar pattern are repeated, as shown in FIG. 2B. The animation in each trial follows the same synchronized pattern as described above, except that minor details of the animation are altered to enhance engagement of the subject's attention. For example, variations between trials may include different types or colors of objects.

In the example shown in FIG. 2B, a batch 240 of fifteen trials is shown in which twelve trials include sounds presented at four different frequencies and three different amplitudes per frequency. For example, test sounds 220, 224, 228 are a 20 dB 0.5 kHz pulse, a 30 dB 1 kHz pulse, and a 40 dB 2 kHz pulse. Also shown are catch trials where no sound is presented, indicated by empty pulse envelopes 222, 226, 230. When a catch trial is added, it does not replace a sound trial, but displaces the sound trial. In an example examination, sounds may be presented in multiple batches, where each batch contains of 30 trials, comprising 20 sound trials (five different frequencies at 4 levels each) and 10 interspersed catch (no-sound) trials. Catch trials preferably represent about ⅓ of the total trials. The presentation of different sounds is randomized in the trials.

The sounds in different trials may have different frequencies and loudness. For example, center frequencies may be 0.5, 1, 2, 4, and 8 kHz, each of which may be presented at 4 different levels of 10, 20, 30, and 40 dB $SPL_A$. These auditory stimuli are presented at regular intervals in phase with the animation, e.g., at the same time that the object reaches its highest point on the screen.

In another example examination, sounds may be presented in batches of up to 60 trials, using an 'ascending-series order', where sounds at the first frequency are presented at 20 dB, incrementing by 10 dB $SPL_A$ until a response is detected. The series terminates at 70 dB, or whatever amplitude a response is detected, and presentations of the next frequency commence. Paralleling standard clinical practice, if a child shows a PDR at 20 dB $SPL_A$ at a given test frequency, the threshold is recorded as 20 dB $SPL_A$. On the other hand, if no significant PDR is observed at any or all frequencies, then the amplitude is increased in 10 dB steps, stepping up the ladder to a maximum of 70 dB $SPL_A$ to determine the elevated threshold. Frequencies from 0.5-4 kHz will be tested in octave steps; the 2 kHz band is given priority. For infants with elevated thresholds, where high sounds levels are required, quieter sounds will be omitted in repeat ladders, shortening the session. At most, each frequency 'ladder' will comprise 6 trials from 20 to 70 dB; most ladders will be shortened on subsequent repeats. If 15 of the 60 trials are set aside as catch trials, 45 trials will be available for measurement of sound-elicited dilations, yielding multiple repeat measurements of each frequency-amplitude combination. Thus, each frequency can be tested multiple times, while still allowing for a large number of catch trials. If any hearing loss is detected, its severity can be determined by accumulating data across the first batch, and if necessary, subsequent 4-min batches.

To compute pupil sizes objectively, we record pupil sizes during trials in which a test sound was presented and during catch trials, which have no sound. The catch trials are incorporated in the examination to determine how much the pupils changed in size when no sounds are presented. The results from these catch trials are used as a reference against which pupil size obtained with a test sound is compared.

During the display of the animation and presentation of the synchronized sounds, images of the eyes of the subject are recorded by a video camera, where the video is precisely synchronized with the animation and sound. The video capture frame rate is preferably at least 20 to 30 fps, which is above the required frame rate for the hardware and video codec used. Using a camera that is sensitive to IR wavelengths has several advantages. First, since humans cannot see IR, an IR spotlight is used to increase illumination of the subject without causing the pupils of the subject to constrict, whereas a visible spectrum spotlight would cause a pupil constriction. Second, at IR wavelengths, irises of all colors appear gray, providing high contrast with the black pupil. At visual wavelengths, dark colored irises would have very low contrast with the black pupil, making image recognition of pupil size difficult. Third, IR sensors are less likely to be impacted by unexpected changes in ambient light from fluorescent or LED lights.

For each video frame, the image is processed to recognize the pupil and calculate its diameter. If the subject is an adult and the head can be immobilized, image recognition of the pupil and calculation of pupil size can be performed using commercially available techniques. In the case of infants, where it is not practical to immobilize the head for the duration of the examination, the infant's attention is drawn to a frontal screen showing a simple animation.

In one embodiment, calculation of pupil size where head movement may take place involves the following steps:
1. The pupil is located within each frame, using computer vision algorithms that locate a dark circular shape within a frame.
2. The pupil image shape, e.g., major and minor axes, diameter, center of mass, and circumference are extracted.
3. Pupil size and location is tracked from frame to frame. Changes in location of the center of the pupil are tracked across frames, yielding information about translation of the pupil on the camera sensor.
4. Movements orthogonal to axis of the lens, i.e., head and eye movements away from the camera, are identified, as described in #3 above. In addition, the ratio of major and minor axes of the pupil indicates the direction of gaze: when the ratio is 1, both axes are identical, and gaze is directed directly towards the camera. When gaze is directed off-center, the diameter orthogonal to direction of movement stays constant, while the diameter parallel to direction of movement shrinks. Finally, gaze direction is also determined by relative displacement between the center of the pupil, and the reflection of the IR spotlight from the cornea. Since the IR spotlight is located centrally, any movement of an eye towards the midline results in the reflection of the spotlight moving closer to the center of the pupil and vice versa. All three of these methods are used to determine gaze direction, and thereby to compensate for distortions in circularity of the pupil arising from head and eye movements. Direction and magnitude of changes in pupil shape are determined by agreement between at least two of the three methods.
5. Movements along the axis of the lens, i.e., head movement toward or away from the camera, are identified. Such movements are particularly important when the infant's movements are less constrained, such as in a parent's lap. These movements result in a change in inter-pupil distance, when both pupils are visible, and in the change in size of other facial features, such as iris size—not pupil size—which can be used even when only one pupil is visible.
6. Computed pupil size is adjusted to compensate for eye and head movements described in #2 to #5 above.
7. Detecting loss of effective imaging of the pupil due to blinks or extremely eccentric gaze direction are identified, and such trials are discarded.
8. Changes in pupil size immediately following sound presentation are examined to determine whether or not a dilation resulted. Dilations are determined by a consistent, frame-to-frame increase in pupil size lasting at least 0.5 seconds. Direct size analysis is complemented by deconvolution and correlation analysis. Consensus between these two methods is required to determine whether a dilation was, in fact, present.

Figure 3:
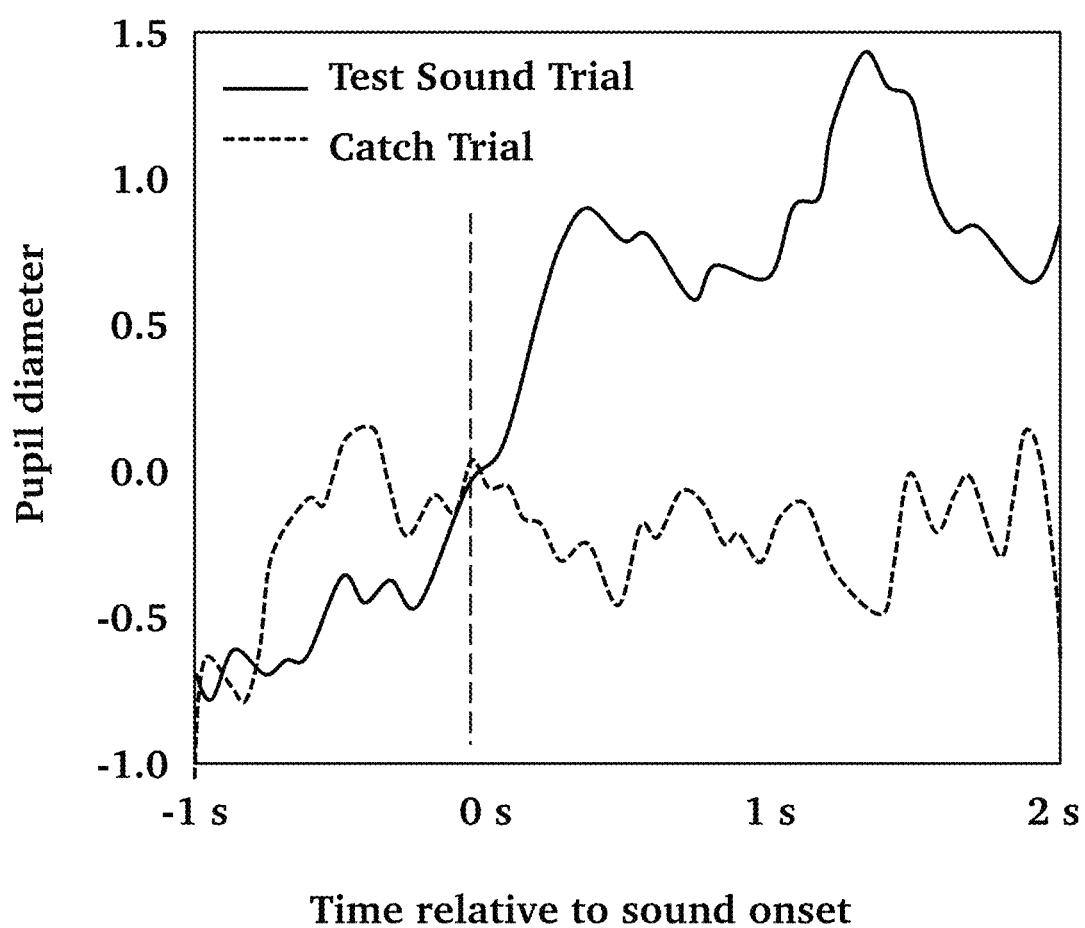
FIG. 3 is a graph of measured pupil diameter as a function of time for a test sound trial superimposed on that for a catch trial according to an embodiment of the invention.

The results of a trial with a 6 month infant is shown in FIG. 3, which plots the average (4 trials) pupil size against time. Time is relative to the start of the second interval of the trial, i.e., 1 second into the trial. For test sound trials, this coincides with the onset of a 2 kHz narrowband noise burst at the level of a quiet conversation, about 50 dB above threshold. The pupil sizes obtained in the catch trials (11 trials) are also shown. After the onset of the sound, the pupil size shows a clear increase, indicating dilation. In contrast, the size during catch trials, which have no sound, shows no such sign of dilation.

In one embodiment, the magnitude of PDR is quantified by computing the area under the graph of pupil diameter with respect to time during the 2 second interval starting at sound onset 1 second into the trial. In other embodiments, the integration was over the 1.75 second interval from 0.25-2 seconds after sound onset. The difference in average pupil sizes obtained in catch and sound trials is further quantified by computing the statistical chance that a significant dilation will occur even when there is no sound. It is relevant to note that, when the amplitude of the presented sound is lower, the PDR is smaller compared to when the amplitude of the sound is higher. Thus, as the PDR decreases in size for quieter presented sounds, the chances increase that a no-sound condition (catch trial) will yield a dilation that approaches those obtained with the quiet sound. When the PDR obtained with a quiet sound and in a catch trial are no longer distinguishable, we infer that the quiet sound was not heard, and that therefore, the subject's hearing threshold is somewhere between the quietest sound that elicited a statistically significant dilation and the amplitude of the quiet sound that did not yield such a dilation.

Pupil diameters at the same relative phase within each trial period are averaged across several trial periods that have sound and separately across several catch trials. If the average dilation with a sound is statistically larger than without, we conclude that a sound was heard.

There are various ways to compare the catch trials with the test trials. These may include simple statistical tests (e.g., t-test), tests based on signal detection theory (SDT), and methods that detect the dynamics of a response such as deconvolution or component analysis. Objectively assessing the significance of any sound-induced change in pupil size preferably uses methods based on SDT.

The presence of a dilation during each trial period is determined after each sound trial by comparing results to several catch trial periods, which do not have sound. During real-time analysis, such single-trial determinations are used as a Yes/No determination to change from one sound frequency to another, as in FIG. 2B.

However, after the completion of a session, the 'audiogram', representing thresholds for the infant across all frequencies tested, is determined by comparing not single-trial data, but averaged data. All trials with a particular frequency-amplitude combination are pooled, and pupil size compared to pupil size data from pooled catch trials. This comparison uses methods based on signal-detection theory, which are relatively conservative and non-parametric, being free of assumptions about the type of statistical distributions that are sampled during the testing session.

Once the video has been analyzed, results along with stimulus parameters can be recorded, stored, transmitted, displayed, and/or otherwise communicated to a device operator such as a clinician.

An overview of the method is outlined in FIG. 4. In step 400, a visually engaging video containing periodic changes is presented on a display. In step 402, sounds synchronized to be in phase with the periodic changes of the video are presented. In step 404, images from an IR camera directed toward the face of a subject positioned in front of the display are recorded to capture images of a subject's eyes. In step 406, the images are processed to measure pupil sizes represented in the images. In step 408, the measured pupil sizes are processed to determine, statistically, the presence of a PDR to the sound.

We also tested the effects of repeating a stimulus on the habituation of the PDR. Results showed that habituation can be minimized by operating at near-threshold stimulus levels.

At sound levels well above threshold, the PDR habituated and could then be recovered by changing the frequency or amplitude of the sound. Consequently, measurement of PDR using the methods of the present invention can also be used to test stimulus discrimination. Given these features, the PDR may be used as an audiometric tool or as a means of assessing auditory discrimination in those who cannot produce a reliable voluntary response.

By replacing the presentation of alternating sounds and silence in different trials with the presentation of two similar phonemes (e.g., /la/ vs /ra/) in different trials, the technique can be used to assess phoneme discrimination. Similarly, by presenting words spoken by different speakers with and without noise, speech detection and speaker identification can be assessed before and after clinical interventions such as speech therapy, hearing aids or cochlear implants. This is a habituation-recovery paradigm. If a sound (habituating stimulus or HS) is repeated, the PDR elicited by later presentations is smaller than responses to the initial presentation. In fact, there is a significant drop from the first to the second presentation. Further repetition causes the PDR to diminish even more. This is true when sounds are more than 20 dB above threshold, and are easily audible to the subject.

Once the PDR is habituated, we can present another sound, the Recovery sound (RS). If the RS is perceived as different or novel, it will elicit a PDR. If the subject cannot tell the difference between the HS and RS, the PDR will be similar to that evoked by HS.

The size of the PDR will depend on how different the RS is perceived to be. When the habituating sound (HS) and RS differ in a simple, easily defined physical parameter, such as intensity, the size of the PDR elicited by the RS is proportional to the difference between the two sounds.

Thus, a habituation-recovery paradigm can potentially be exploited as a reporting tool to examine discrimination by habituating the PDR with one set of stimulus parameters and testing for recovery by altering one of the parameters, an approach we have previously used to determine auditory discrimination thresholds in barn owls (Bala and Takahashi 2000; Bala et al. 2003, 2007; Spitzer et al. 2003).

In other cases, such as speech sounds, the difference between any sounds is perceptual rather than parametric. For example, in babies raised by native English-speaking parents, the syllables /ra/ and /la/ are perceived as different, while in babies raised by native Japanese-speaking parents, the two sounds are perceptually indistinguishable. Thus, the recovery elicited by an RS depends on how different the RS is from the HS perceptually, rather than a difference that is defined by acoustical parameters. This is especially true when speech sounds are involved.

The habituation-recovery paradigm has important applications, including assessing the efficacy of interventions in infants diagnosed with hearing loss. As described above, infant hearing tests aim to meet the 1-3-6 guidelines. In an ideal world, if hearing loss is diagnosed, interventions can be in place when infants are 6 months or older. Hearing aids, as well as cochlear implants, are now routinely prescribed for infants. However, both these interventions must, as in adults, be customized for optimal use. In adults, such optimization uses interactive testing, allowing tuning for better speech perception. In the case of infants, of course, such optimization is impossible, and must instead wait until infants are 3 to 4 years old. Thus while interventions are possible, these interventions cannot be assayed for efficacy.

The PDR offers a way to make such tests possible. The habituation-paradigm can test for optimizations of hearing aids and cochlear implants that maximize speech perception. Examples are probing phoneme discrimination, speech vs non-speech sound discrimination, which, after all, is the main goal of early intervention. Habituation-recovery can even be used to test infant's ability to discriminate between adult-directed speech ('adultese') and infant-directed speech ('infantese'): infants have been shown to attend to the latter more than the former. This is one major lacuna in infant hearing tests, and offers a solution that currently does not exist.

The invention claimed is:

1. A method for measuring pupil dilation response to sound, the method comprising:
    presenting on a display to a subject a visually engaging video containing an animation having periodic changes;
    presenting to the subject sounds at regular intervals in phase with the periodic changes of the animation;
    recording images of an eye of the subject from a camera directed toward eyes of the subject, where the camera is sensitive to infrared wavelengths;
    processing the images to measure pupil sizes of a pupil of the eye of the subject, wherein processing the images comprises extracting major and minor axes of the pupil in each of the images and adjusting pupil size and shape to compensate for head and eye movements;
    processing the measured pupil sizes to determine, statistically, the presence of a pupil dilation response to the sounds.

2. The method of claim 1 wherein the visually engaging video is selected to have sufficiently constant luminance to avoid pupil responses to luminance changes.

3. The method of claim 1 wherein the visually engaging video is selected to be sufficiently engaging such that a child's gaze remains focused on the animation during a majority of a predetermined examination time.

4. The method of claim 1 wherein the visually engaging video includes periodic patterns sufficiently repetitive to cause habituation.

5. The method of claim 1 wherein the sounds are selected to cause a pupil dilation response without causing a startle response.

6. The method of claim 1 wherein processing the measured pupil sizes to determine the presence of a pupil dilation response comprises comparing pupil sizes in trial periods with test sounds against pupil sizes in trial periods without test sounds.

7. The method of claim 1 wherein processing the images to measure pupil sizes comprises tracking pupil location from frame to frame, extracting major and minor axes of the pupil, identifying head and eye movements, and adjusting pupil size and shape to compensate for the identified head and eye movements.

* * * * *